(12) United States Patent (10) Patent No.: US 8,577,081 B2
Kelusky et al. (45) Date of Patent: *Nov. 5, 2013

(54) MOBILE VIDEO-BASED THERAPY

(75) Inventors: Ronald L. Kelusky, Markham (CA); Scott Robinson, Whitby (CA)

(73) Assignee: Qualcomm Incorporated, San Diego, CA (US)

( * ) Notice: Subject to any disclaimer, the term of this patent is extended or adjusted under 35 U.S.C. 154(b) by 70 days.

This patent is subject to a terminal disclaimer.

(21) Appl. No.: 13/316,424

(22) Filed: Dec. 9, 2011

(65) Prior Publication Data

US 2012/0082353 A1 Apr. 5, 2012

Related U.S. Application Data

(63) Continuation of application No. 12/112,573, filed on Apr. 30, 2008, now Pat. No. 8,094,873.

(60) Provisional application No. 60/915,091, filed on Apr. 30, 2007.

(51) Int. Cl.
*G06K 9/00* (2006.01)
*A61H 1/00* (2006.01)

(52) U.S. Cl.
USPC ............................... 382/100; 382/291; 601/5

(58) Field of Classification Search
USPC ......... 382/100, 103, 106–107, 118, 123, 128, 382/155, 162, 168, 173, 181, 189–194, 199, 382/209, 219, 232, 254, 274, 276, 286–294, 382/305, 312, 318; 345/156; 601/5; 600/595; 482/4
See application file for complete search history.

(56) References Cited

U.S. PATENT DOCUMENTS

| | | | |
|---|---|---|---|
| 5,745,165 A | 4/1998 | Atsuta et al. | |
| 6,007,459 A | 12/1999 | Burgess | |
| 6,160,899 A * | 12/2000 | Lee et al. | 382/103 |
| 6,244,987 B1 * | 6/2001 | Ohsuga et al. | 482/4 |
| 6,827,579 B2 | 12/2004 | Burdea et al. | |
| 6,996,261 B2 | 2/2006 | DeCharms | |
| 7,018,211 B1 | 3/2006 | Birkholzer et al. | |
| 7,227,526 B2 * | 6/2007 | Hildreth et al. | 345/156 |
| 7,259,747 B2 | 8/2007 | Bell | |
| 7,264,554 B2 | 9/2007 | Bentley | |
| 7,402,743 B2 | 7/2008 | Clark et al. | |
| 7,515,734 B2 | 4/2009 | Horovitz et al. | |
| 7,918,808 B2 | 4/2011 | Simmons | |

(Continued)

OTHER PUBLICATIONS

International Search Report and Written Opinion—PCT/US2008/062065, International Search Authority—European Patent Office—Sep. 2, 2008.

*Primary Examiner* — Seyed Azarian
(74) *Attorney, Agent, or Firm* — Kilpatrick Townsend & Stockton LLP

(57) ABSTRACT

Mobile video-based therapy, using a portable therapy device that includes a camera, a therapy application database, a processor, and a display. The camera is configured to generate images of a user, and the therapy application database is configured to store therapy applications. The processor is configured to select, from the therapy application database, a therapy application appropriate for assisting in physical or cognitive rehabilitation or therapy of the user, to invoke the therapy application, to recognize a gesture of the user from the generated images, and to control the invoked therapy application based on the recognized gesture. The display is configured to display an output of the controlled therapy application.

25 Claims, 9 Drawing Sheets

(56) References Cited

U.S. PATENT DOCUMENTS

| | | |
|---|---|---|
| 2003/0120183 A1* | 6/2003 | Simmons .................... 600/595 |
| 2005/0239028 A1 | 10/2005 | Wu et al. |
| 2006/0101016 A1 | 5/2006 | Uehara |
| 2006/0204045 A1 | 9/2006 | Antonucci |
| 2007/0098250 A1 | 5/2007 | Molgaard et al. |
| 2008/0089587 A1 | 4/2008 | Kim et al. |
| 2009/0062698 A1* | 3/2009 | Einav et al. .................... 601/5 |
| 2010/0062403 A1 | 3/2010 | Williams et al. |
| 2010/0117837 A1 | 5/2010 | Stirling et al. |
| 2010/0209007 A1 | 8/2010 | Elyada et al. |
| 2011/0044501 A1 | 2/2011 | Tu et al. |

* cited by examiner

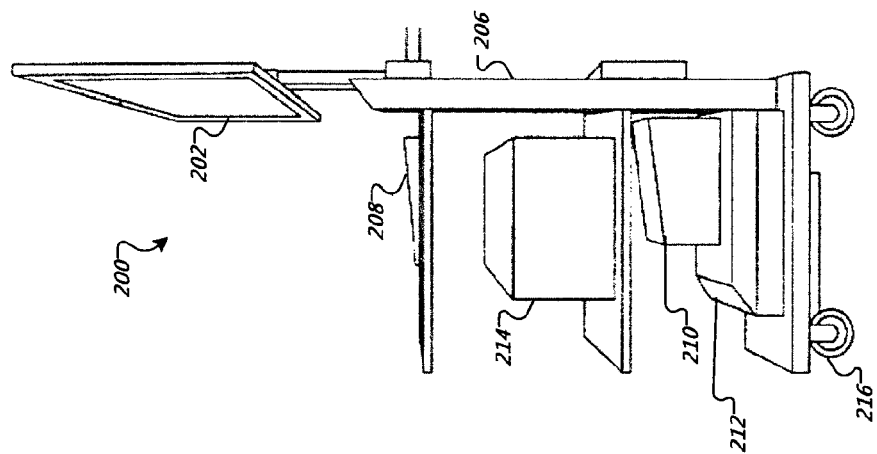
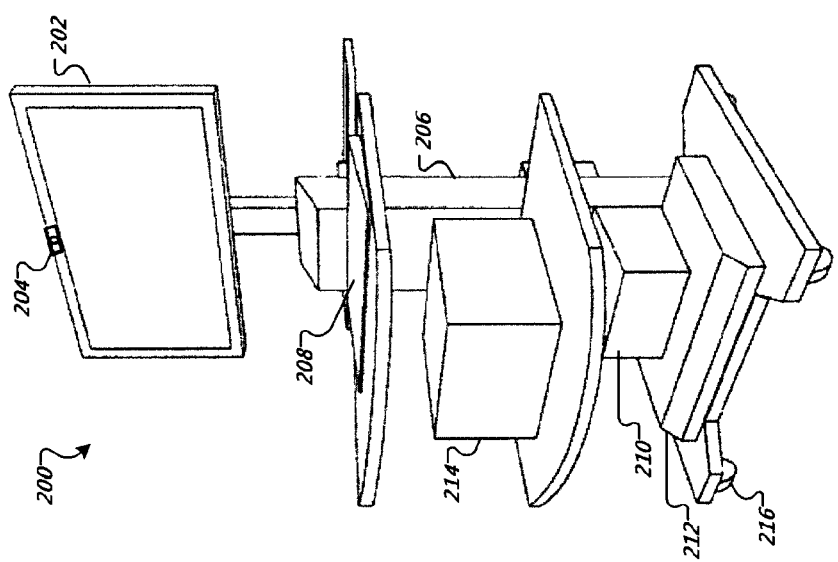
FIG. 2

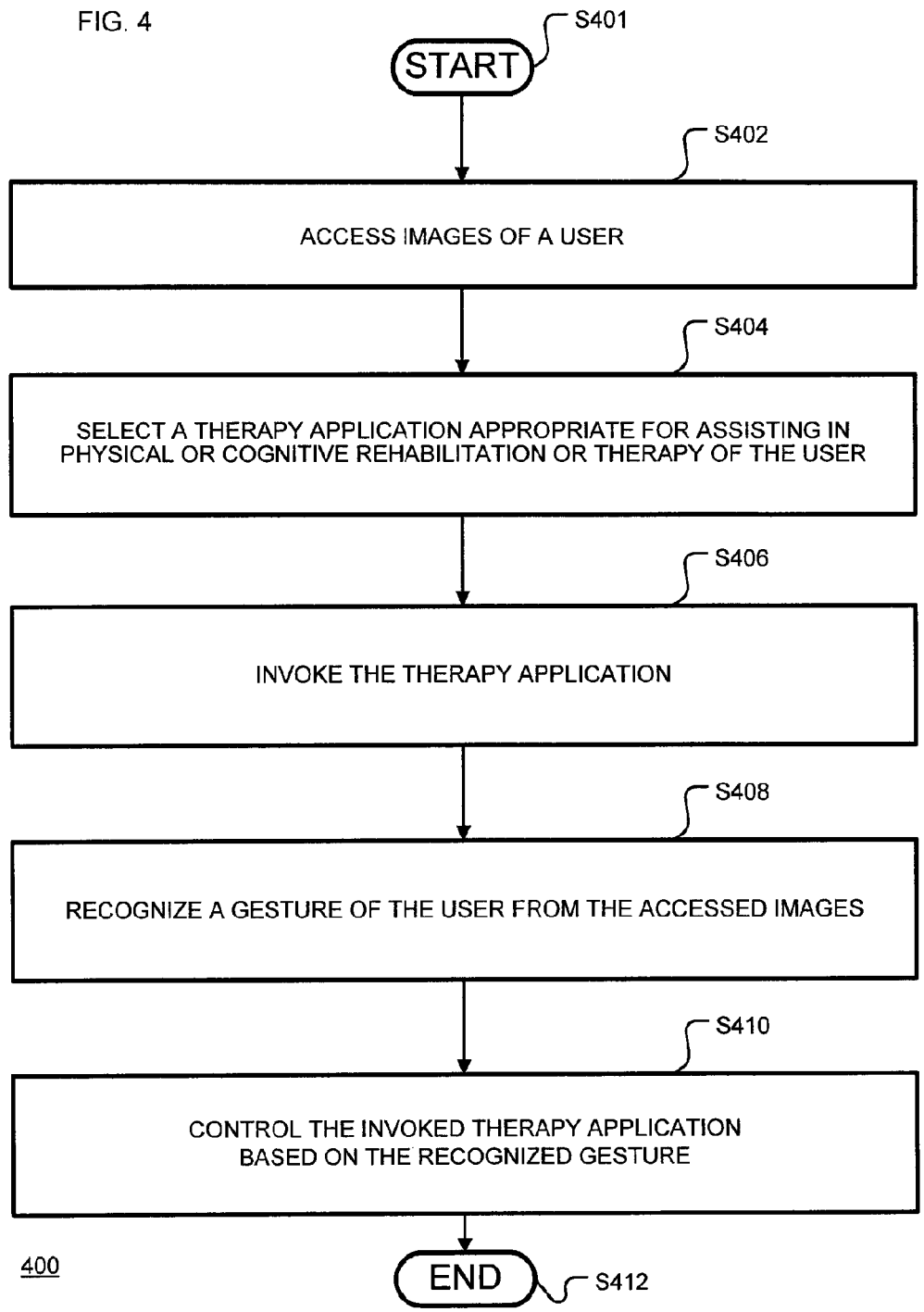

| | PLAYMERSION | | | | | | | | MY MUSIC WORLD | | | | | | |
|---|---|---|---|---|---|---|---|---|---|---|---|---|---|---|---|
| | SOCCER | NINJA | WIZARDS CAVERN | ORBOSITY | COCONUT SHOOTER | SHARK | VOLLEY BALL | JUGGLER | DRUMS | HORNS | FARM ANIMALS | TAMBOURINE | DANCE | MY MUSIC COMPOSER | SENSORY WORLD |
| PHYSICAL THERAPY | | | | | | | | | | | | | | | |
| UPPER BODY | | | | | | | | | | | | | | | |
| HEAD/NECK | | X | X | X | X | X | X | X | X | X | X | X | X | X | X |
| BACK | | | X | | X | | X | | | | | | | | X |
| SHOULDERS | | | X | | X | | X | | | | | | | | X |
| ARMS | | | X | | X | | X | | | | | | | | X |
| ELBOW | X | X | X | X | | | X | X | X | X | X | X | X | X | X |
| WRISTS | | X | X | X | | | X | X | X | X | X | X | X | X | X |
| TORSO | | | X | | X | X | | | | | | | | | |
| REACHING | | X | X | X | | | X | X | X | X | X | X | X | X | X |
| LOWER BODY | | | | | | | | | | | | | | | |
| LOWER BACK | X | | X | | | | X | | | | | | | | |
| LEGS | X | | X | | | | X | | | | | | | | |
| FEET/ANKLES | X | | X | | | | X | | | | | | | | |
| FULL BODY | | | | | | | | | | | | | | | |
| BENDING | X | | | | | X | X | | | | | | | | |
| BODY REACHING | X | | | | | X | X | | | | | | | | |
| SIDE TO SIDE | X | | X | | | X | X | | | | | | | | |
| BALANCE | X | | X | | | X | X | | | | | | | | |
| POSTURAL CONTROL | | | | | | | | | | | | | | | |
| FINE MOTOR | | | | | | | | X | | | | | X | | |
| WEIGHT SHIFTING | X | X | X | X | | X | X | | | | | | | | |
| TWISTING | | X | X | | | X | X | | | | | | | | |
| CORE STRENGTH | | | X | | | X | X | | | | | | | | |

610

| | SOCCER | NINJA | WIZARDS CAVERN | ORBOSITY | COCONUT SHOOTER | SHARK | VOLLEY BALL | JUGGLER | DRUMS | HORNS | FARM ANIMALS | TAMBOURINE | DANCE | MY MUSIC COMPOSER | SENSORY WORLD |
|---|---|---|---|---|---|---|---|---|---|---|---|---|---|---|---|
| COGNITIVE THERAPY | | | | | | | | | | | | | | | |
| LEARNING | X | X | X | X | X | X | X | X | X | X | X | X | X | X | |
| SELF EXPRESSION | | | X | X | | | | | X | X | X | X | X | X | X |
| CREATIVITY | | | X | X | | | | | X | X | X | X | X | X | X |
| ACHIEVEMENT/MASTERY | X | X | X | X | X | X | X | X | X | X | X | X | X | X | X |
| SENSORY STIMULATION | | | | | | | | | | | | | | X | X |
| SOCIALIZATION | | | | | | | | X | | | | | | | |
| RELAXATION | | | | X | | | | | | | | | | | X |
| COMMUNICATION | | | | | | | | | X | X | | X | | X | X |
| EMOTIONAL EXPRESSION | X | X | X | | X | X | X | X | X | X | X | X | X | X | X |
| AUDIOVISUAL STIMULATION | X | X | X | X | X | X | X | X | X | X | X | X | X | X | X |
| PERCEPTUAL MOTOR SKILLS | X | X | X | X | X | X | X | X | X | X | X | X | X | X | X |
| SENSORY MOTOR SKILLS | X | X | X | X | X | X | X | X | X | X | X | X | X | X | X |
| VARIETY | X | X | X | X | X | X | X | X | X | X | X | X | X | X | X |
| CONCENTRATION | X | X | X | X | X | X | X | X | X | X | X | X | X | X | |
| SELECTION RECOGNITION | X | X | X | X | X | X | X | X | X | X | X | X | X | X | X |

605 / 620 / 630

MOBILE VIDEO-BASED THERAPY

CROSS-REFERENCE TO RELATED APPLICATION

This application is a continuation of U.S. patent application Ser. No. 12/112,573, filed Apr. 30, 2008, and entitled "Mobile Video-Based Therapy," which claims the benefit of U.S. Provisional Patent Application No. 60/915,091, filed Apr. 30, 2007, and all of the foregoing applications are incorporated herein by reference in their entireties for all purposes.

FIELD

The present disclosure generally relates to computer-based therapy.

BACKGROUND

Medical facilities, such as hospitals, employ various therapy devices for assisting in treatment of patients. These devices often require involvement by medical staff for proper operation. In addition, these devices often require handling by the patient, which may result in contamination of the equipment. Therapy devices may also be difficult to move from patient to patient, and they may be limited in their ability to provide different, condition-specific therapies as well as guidance for choosing particular therapies.

SUMMARY

According to one general implementation, a mobile therapy cart captures images of a patient using an on-board camera, and selects and controls one of several certified and proven physical or cognitive therapy applications based on the user's gestures, which are automatically detected from the captured images. In doing so, the mobile therapy cart provides a low-cost, multiple use therapy device that may be shared amongst many patients, achieving a high rate of use. By accepting camera-based inputs, the patents are not required to physically touch the mobile therapy cart, minimizing the hazardous spread of germs within a hospital environment.

According to another general implementation, a portable therapy device includes a camera, a therapy application database, a processor, and a display. The camera is configured to generate images of a user, and the therapy application database is configured to store therapy applications. The processor is configured to select, from the therapy application database, a therapy application appropriate for assisting in physical or cognitive rehabilitation or therapy of the user, to invoke the therapy application, to recognize a gesture of the user from the generated images, and to control the invoked therapy application based on the recognized gesture. The display is configured to display an output of the controlled therapy application. The therapy application may be selected and controlled without requiring the user to touch the portable therapy device.

According to another general implementation, a computer-implemented process includes accessing images of a user, and selecting a therapy application appropriate for assisting in physical or cognitive rehabilitation or therapy of the user. The process also includes invoking the therapy application, recognizing a gesture of the user from the accessed images, and controlling the invoked therapy application based on the recognized gesture.

Implementations may include one or more of the following features. For example, a medical condition of the user may be determined, where the therapy application may be selected based on the determined medical condition. Selecting the therapy application may further include accessing a matrix correlating therapy applications with medical conditions and therapeutic effects, inputting the determined medical condition or a desired therapeutic effect remedying the determined medical condition into the matrix, accessing, as an output of the matrix, a set of therapy applications correlating to the determined medical condition or the desired therapeutic effect, and selecting the therapy application from the accessed set of therapy applications. Determining a medical condition of the user may further include determining an identity of the user based on performing facial detection and recognition on one of the accessed images, and querying a database that correlates users with medical conditions, using the determined identity. Determining the medical condition of the user may further include detecting that the user has suffered a stroke, and selecting the therapy application may further include selecting a hand-eye coordination therapy application.

In another example, determining the medical condition of the user may further include recognizing a medical appliance in one of the images, and correlating the medical appliance to the medical condition. In another alternative, determining the medical condition of the user may further include determining, from one of the images, a position or orientation of the user, and correlating the position or orientation to the medical condition. Determining the medical condition of the user may also further include receiving, from a medical professional user other than the user, a selection of the medical condition of the user. Determining the medical condition of the user may further include performing an optical character recognition on a portion of one of the images, recognizing, from the portion, a word based on performing the optical character recognition, and matching the recognized word with the medical condition.

In additional examples, invoking the therapy application further includes generating a virtual environment, and displaying a representation of the user within the virtual environment, recognizing the gesture may further include recognizing a magnitude and direction of the gesture, and controlling the selected therapy application may also include moving the representation within the virtual environment in a magnitude and direction correlating to the determined magnitude and direction of the gesture, and providing visual or audible feedback to the user based on moving the representation. The therapy application may include a music therapy application, a sports therapy application, or an immersive gaming therapy application.

In further examples, recognizing the gesture may further include recognizing wave gesture above a head of the user, and controlling the invoked therapy application may further include starting or stopping the invoked therapy application. Controlling the invoked therapy application may further include interacting with a virtual object in a virtual world defined by the therapy application. Controlling the invoked therapy application may further include enabling a user to play a song or portion of a song using the recognized gesture. Controlling the invoked therapy application may further include mapping the recognized gesture to a mouse event. Selecting the therapy application may further include recognizing, from one of the images, whether the user possesses a controller, selecting a first therapy application that requires possession of the controller, if the user is recognized to possess the controller, and selecting a second therapy application that does not require possession of the controller, if the user is recognized to not possess the controller. Selecting the therapy application may further include displaying icons each representing a candidate therapy application, adjacent to an avatar, recognizing, from the accessed images, a gesture of the user, controlling the avatar based on the recognized gesture, and outputting, as the selected therapy application, the candidate therapy application whose icon is affected by the controlled avatar.

In another general implementation, a computer-readable medium is encoded with a computer program. The computer program includes instructions that, when executed, cause a computer to perform operations including accessing images of a user, and selecting a therapy application appropriate for assisting in physical or cognitive rehabilitation or therapy of the user. The computer program also includes instructions that, when executed, cause the computer to perform operations including invoking the therapy application, recognizing a gesture of the user from the accessed images, and controlling the invoked therapy application based on the recognized gesture.

This brief summary has been provided to enable a quick understanding of various concepts and implementations described by this document. A more complete understanding may be obtained by reference to the following detailed description in connection with the attached drawings. It is to be understood that other implementations may be utilized and changes may be made.

BRIEF DESCRIPTION OF THE DRAWINGS

FIGS. 2 and 8 illustrate exemplary therapy devices.
FIG. 4 is a flowchart of an exemplary process.
FIG. 6 illustrates a therapy matrix.

DETAILED DESCRIPTION

According to one general implementation, a mobile therapy cart captures images of a patient using an on-board camera, and selects and controls one of several certified and proven physical or cognitive therapy applications based on the user's gestures, which are automatically detected from the captured images. In doing so, the mobile therapy cart provides a low-cost, multiple use therapy device that may be shared amongst many patients, achieving a high rate of use. By accepting camera-based inputs, the patents are not required to physically touch the mobile therapy cart, minimizing the hazardous spread of germs within a hospital environment.

Thus, an enhanced approach is provided for capturing a user's gesture in the space surrounding their body ("freespace") with a camera, recognizing the gesture, and using the gesture as a user input to control a therapy device. A camera such as a depth camera may be used to control a therapy device based on the recognition of gestures or changes in gestures of a user. Unlike touch-screen systems that may suffer from cross-patient contamination and the deleterious, obscuring effect of fingerprints, gesture-based input allows a device to be controlled based on the user's natural body movements or poses.

As used herein throughout, a "gesture" is intended to refer to a form of non-verbal communication made with part of a human body, and is contrasted with verbal communication such as speech. For instance, a gesture may be defined by a movement, change or transformation between a first position, pose, or expression and a second pose, position or expression. Common gestures used in everyday discourse include for instance, an "air quote" gesture, a bowing gesture, a curtsey, a cheek-kiss, a finger or hand motion, a genuflection, a head bobble or movement, a high-five, a nod, a sad face, a raised fist, a salute, a thumbs-up motion, a pinching gesture, a hand or body twisting gesture, or a finger pointing gesture. A gesture may be detected using a camera, such as by analyzing an image of a user, using a tilt sensor, such as by detecting an angle that a user is holding or tilting a device, or by any other approach.

A body part may make a gesture (or "gesticulate") by changing its position (i.e. a waving motion), or the body part may gesticulate without changing its position (i.e. by making a clenched first gesture). Although the enhanced approach uses, as examples, hand and arm gestures to effect the control of functionality via camera input, other types of gestures may also be used.

Figure 1:
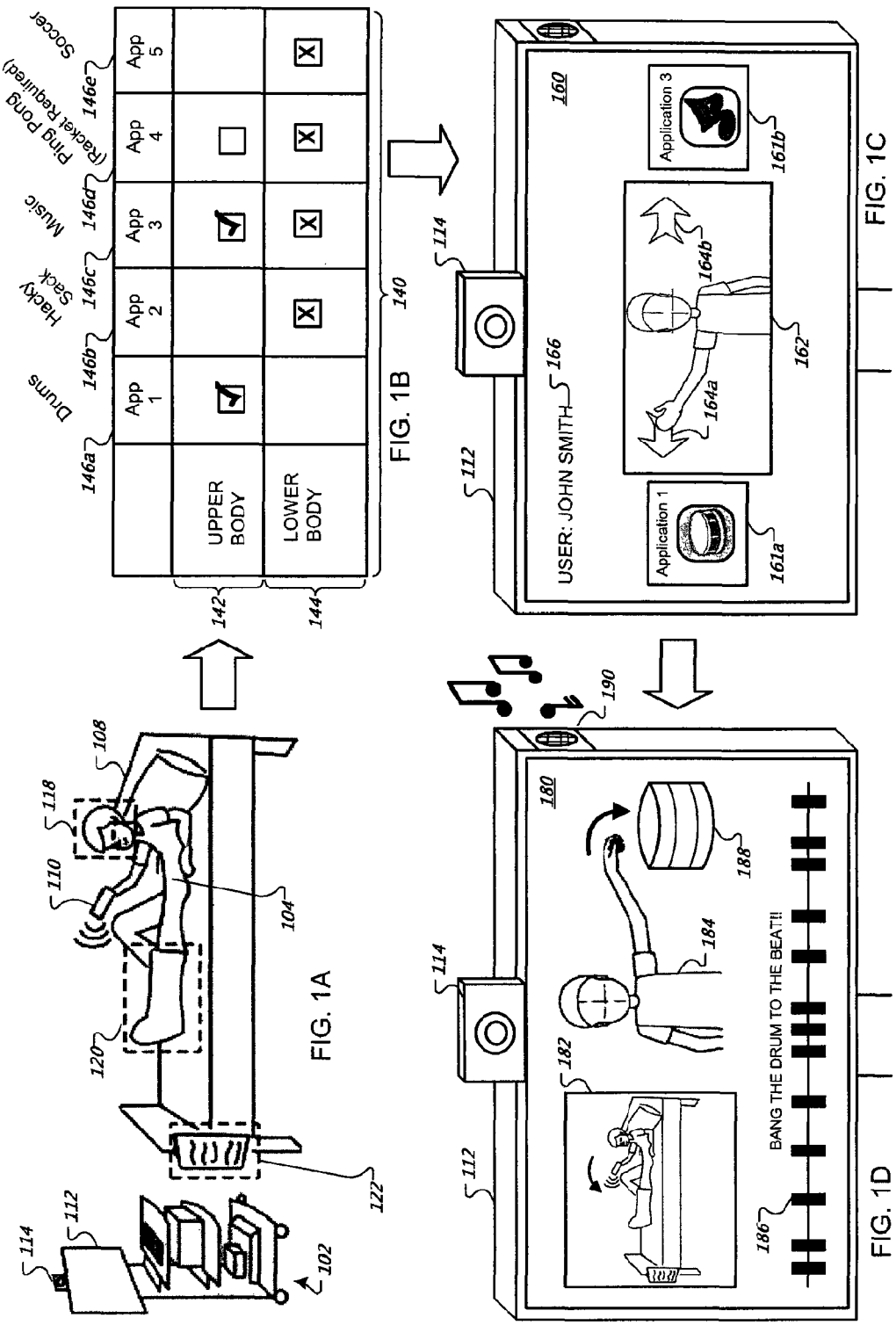
FIGS. 1A-1D are contextual diagrams demonstrating control of a therapy device using recognized gestures.

FIGS. 1A-1D are contextual diagrams demonstrating control of a therapy device 102 using recognized gestures. In FIG. 1A, a patient 104 with a cast on his leg is lying on a bed 108, holding a controller 110. The therapy device 102 has been rolled in front of the bed 108 by a medical professional, such as a physical therapist, or by automatically summoning the therapy device 102 using the controller 110. The therapy device 102 may include a display 112 and camera 114. The display 112 may present a therapy application appropriate for assisting in physical or cognitive rehabilitation or therapy of the patient 104. The camera 114 is configured to generate images of the patient.

The therapy device 102 may invoke the therapy application, recognize gestures of the patient 104 from the generated images, and control the therapy application based on the recognized gestures. The patient 104 may gesture using the controller 110 or by using a physical body part, such as a hand, leg, arm, his head, etc. Gesture-based control allows the therapy device to be selected and controlled without requiring the patient to touch the therapy device, avoiding contamination.

A number of approaches may be used to select a therapy application for the patient 104. The patient 104 or a medical professional may manually select a therapy application using an interface of the therapy device. As another example, an identity of the patient 104 may be determined based on detecting and recognizing the face of the patient 104 in a portion of an image 118. A database (e.g., a hospital or insurance database) may be queried, using the determined patient identity, to determine therapy prescriptions. Therapy applications may be selected, manually and/or automatically, based on the therapy prescriptions. The orientation or position of the patient 104 may also be determined. For example, an orientation (i.e., sitting, standing, lying horizontal) of the patient 104 may be determined, and an appropriate therapy application may be selected based on the determined orientation.

In some implementations, a medical condition of the patient 104 may be determined and an appropriate therapy application may be selected based on the determined condition. For example, if it is determined that the patient 104 has suffered a stroke, a hand-eye coordination therapy application may be selected. A medical professional may manually select or enter one or more medical conditions using an interface of the therapy device.

Medical conditions may also be automatically determined. For example, a medical condition may be determined as a result of the therapy device 102 recognizing a medical appliance in a captured image of the patient. For example, the cast may be recognized from a portion of an image 120, indicating that the patient 104 has a leg injury and resulting in the selection of upper body therapy applications rather than lower body therapy applications. As another example, a wheelchair may be detected and recognized from a captured image, where therapy applications that would be inappropriate to perform in a wheelchair would be excluded from the menu of available therapy applications presented to the user or medical professional.

A medical condition may also be determined, for example, by performing optical character recognition on one or more items within the field of view of the camera (i.e., optical character recognition may be performed on a portion of a captured image). For example, a medical chart or a label on a bottle of medicine may be identified within a portion of an image 122. Optical character recognition may be performed on the image of the medical chart 122 and patient information, such as patient identity and existing medical conditions may be identified from the contents of the medical chart. For example, one or more words may be recognized based on performing optical character recognition, and the recognized word(s) may be matched to one or more medical conditions.

FIG. 1B illustrates a matrix 140 which correlates therapy applications with medical conditions and which may be accessed to select a therapy application. A determined medical condition or a desired therapeutic effect remedying the determined medical condition may be input into the matrix 140. An output of the matrix 140 may be a set of therapy applications correlating to the determined medical condition or the desired therapeutic effect. A therapy application may be selected from the outputted set of therapy applications. If a single therapy application only addresses the determined medical condition, that application may be invoked automatically without further intervention of the user.

The matrix 140 displays upper body applications in a first row 142 and lower body applications in a second row 144. The matrix 140 displays available therapy applications 146 in columns. For example, available therapy applications 146 include a drums application 146a, a hacky-sack application 146b, a music application 146c, a ping pong application 146d, and a soccer application 146e.

In addition to correlating therapy applications and medical conditions, the matrix 140 may also include associations between therapy applications 146 and therapeutic effects or intended uses of the therapy applications 146. For example, the matrix 140 may indicate that a particular application 146 (e.g., the music application 146c) provides a particular type of cognitive therapy (e.g., creativity). The matrix 140 may therefore provide a basis for selecting particular therapy applications 146 for different physical conditions and rehabilitation needs.

The matrix 140 stores, for each application 146, an indication of whether the application 146 is applicable or appropriate for upper and/or lower body therapy. Such an indication may be based on past studies that prove or disprove the effectiveness of a certain therapy to treat a medical condition, or they may be based upon the experience of a medical practitioner. For example, the music application 146c, the soccer application 146e, the ping pong application 146d, and the hacky-sack application 146b may be appropriate for lower body therapy, and the music application 146c, the drums application 146a, and the ping pong application 146d may be appropriate for upper body therapy.

Some applications require the use of a controller or special piece of equipment. For example, the ping pong application 146d may require the use of a ping pong paddle. From captured images, the presence or lack of presence of a required controller may be recognized. The presence or lack of presence of a controller may be provided as an input to the matrix 140. If the patient 104 is recognized to possess a controller, then therapy applications 146 that require possession of the controller may be selected as candidate therapy applications. If the patient 104 is recognized to not possess a controller, then therapy applications 146 that do not require possession of the controller may be selected as candidate therapy applications, and therapy applications that require the possession of the controller may be excluded. For example, the patient 104 may be recognized to not possess a required ping pong controller, and as a result the ping pong application 146d may be excluded from a list of candidate therapy applications, even though the ping pong application 146d may otherwise have been an appropriate application for upper body therapy.

For example, for the patient 104, the medical condition indicated by the cast (i.e. a broken leg) may be inputted into the matrix 140. The medical condition input may result in lower body therapies being excluded from the outputted list of therapy applications applicable for the patient 104. Upper body therapy applications 146a, 146c, and 146d may be considered. The ping pong application 146d, although an upper body application, may be excluded if a required ping pong paddle was not detected. A set of candidate applications, including the drums application 146a and the music application 146c may be provided as an output of the matrix 140.

The selection of a particular application 146 for a particular user may be performed manually or automatically using the matrix 140. In one example, the patient 104 or medical staff may select applications 146 using the matrix 140. Various logic may access the matrix 140 and guide a user in the selection process. One or more front end interfaces (which may be displayed on the display 112) may be associated with the matrix 140. Various software-based modules may generate such interfaces for facilitating user interaction with the matrix 140.

An example interface 160 for selecting one of a plurality of candidate therapy applications is shown in FIG. 1C. The interface 160 may be displayed on the display 112. The interface 160 may present candidate therapy applications to the user for selection (the user may be the patient 104 or may be a medical professional). For example, icons 161a and 161b, representing the drums application 146a and music application 146c, respectively, are presented next to an avatar 162. The interface 160 displays the name 166 of the patient 104 (for example, the patient name may have been queried from a database, such as after a facial recognition process identified the patient 104). In some implementations, a live video image of the user is displayed in place of the avatar 162.

The user may gesture (e.g., with their arm, hand, controller, etc.) to control the avatar 162. Gestures may be recognized form accessed images, and the avatar may be controlled based on the recognized gestures. For example, if the user moves their hand to the left, the avatar's arm may move on the interface 160 to the left and overlap or become adjacent to an interaction element 164a, causing an interaction with the interaction element 164a. The interaction with the interaction element 164a results in the application associated with the icon 161a (i.e., the drums application 146a) being identified as the selected therapy application. If the user gestures to the right, an interaction with an interaction element 164*b* may occur, resulting in that case in the application associated with the icon 161*b* (i.e., the music application 146*c*) being identified as the selected therapy application.

FIG. 1D illustrates the use of a therapy application. The therapy application selected in the interface 160 (e.g., the drums application 146*a*) is displayed in an interface 180. The interface 180 may be displayed on the display 112 (i.e., upon selection of a therapy application using the interface 160, the interlace 160 may be replaced on the display 112 by the interlace 180). The interface 180 includes a representation 182 of the patient 104. For example, in some implementations, the representation 182 displays a live video image of the patient 104.

The interface 180 also includes an avatar 184. The drums therapy application 146*a* allows the patient 104 to control the avatar 184 through gestures. Such an application may stimulate cognitive processes or muscular development, and may be beneficial for a bedridden patient. The patient 104 is prompted to "bang" a drum (e.g., by gesturing downward with a hand or controller), in time with an animated drum line 186 displayed at the bottom of the interlace 180. As the "banging" gestures of the patient 104 are detected, the avatar 184 is controlled to "bang" a virtual drum 188. As the drum 188 is struck by the avatar 184, a drum sound may be played on a speaker 190. Other sounds or music may be played on the speaker 190 along with the drum sounds. The volume of the drum sounds may correspond to the speed and/or magnitude of the patient's associated gesture (i.e., the drum noise may be louder if the user gestures for a longer distance and/or at a faster speed).

FIG. 2 illustrates front and side views of an exemplary therapy device 200. As mentioned above, the therapy device 200 includes a display 202 and a camera 204. The therapy device 200 may also include a mobile support structure 206, a keyboard 208, a power supply 210 and a computing device 212. Other peripheral devices are possible, such as a mouse or a printer. In some implementations, the therapy device 202 includes one or more storage areas 214, for storing controllers and other equipment. The therapy device 200 may include a receiver, for communication with remote controllers. In some implementations, the therapy device 200 may be rolled on wheels 216.

Figure 3:
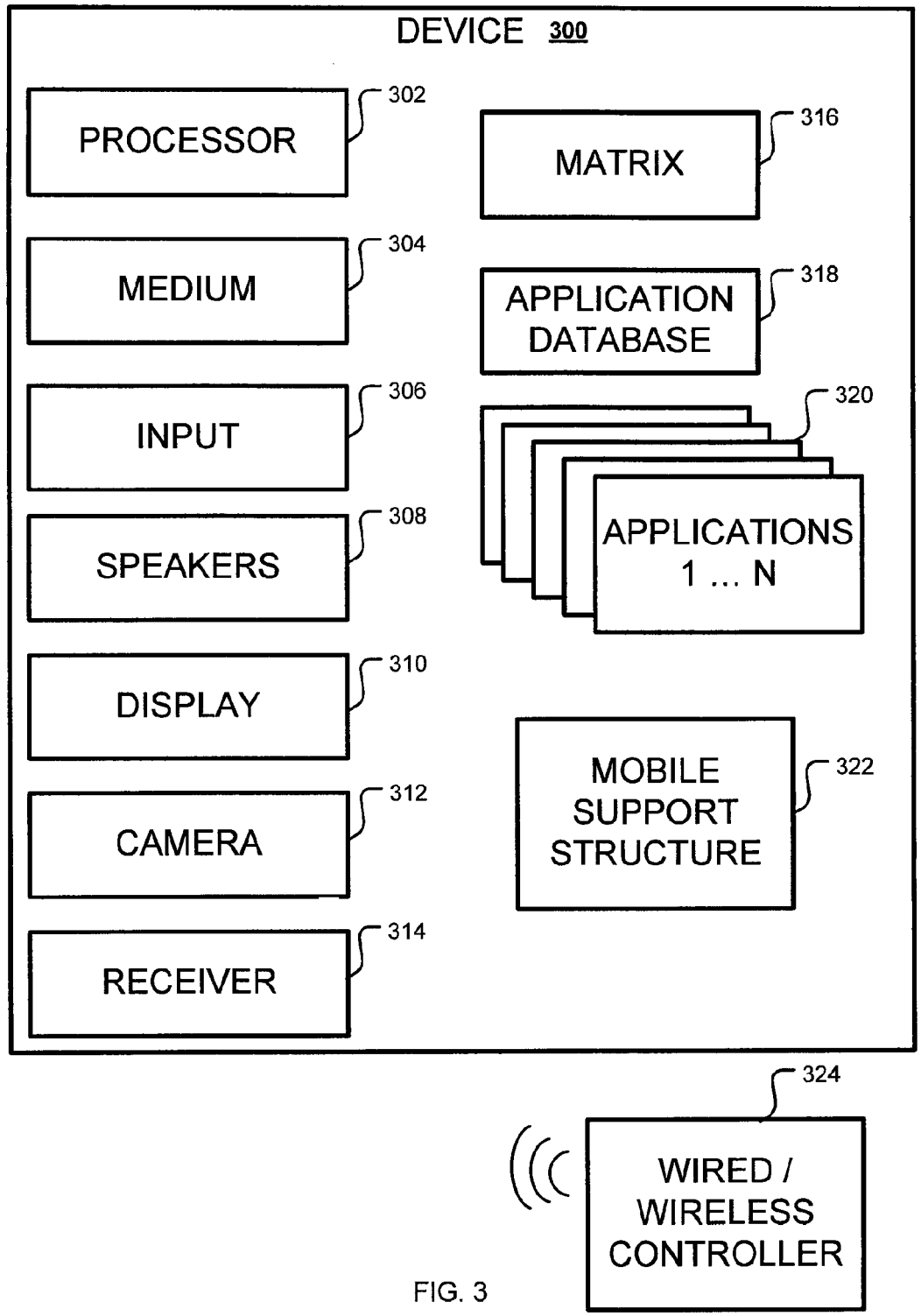
FIG. 3 is a block diagram of an exemplary therapy device.

FIG. 3 is a block diagram of an exemplary therapy device 300. The device 300 includes a processor 302, a storage medium 304, one or more input devices 306, speakers 308, a display 310, a camera 312, a receiver 314, a matrix 316, an application database 318, one or more therapy applications 320, and a mobile support structure 322. The device 300 may communicate over one or more wired or wireless pathways with a controller 324.

The display 310 may allow a user to interact with the device 300, or with applications invoked by the device 300. The display 310 may be configured to render a visual display image. For example, the display 310 may be a monitor, a television, a liquid crystal display (LCD), a plasma display device, a projector with a projector screen, an auto-stereoscopic display, a cathode ray tube (CRT) display, a digital light processing (DLP) display, or any other type of display device configured to render a display image. The display 310 may include one or more display devices. In some configurations, the display 310 may be configured to display images associated with an application, such as display images generated by an application, including an object or representation such as an avatar.

The storage medium 304 stores and records information or data, and may be an optical storage medium, magnetic storage medium, flash memory, or any other storage medium type. The receiver 314 may provide for communication with one or more wired or wireless controllers 324 (such as a ping pong controller). The speakers 308 may provide audio output and feedback to the user.

The camera 312 is a device used to capture images, either as still photographs or a sequence of moving images. The camera 312 may use the light of the visible spectrum or with other portions of the electromagnetic spectrum, such as infrared. For example, the camera 312 may be a digital camera, a digital video camera, or any other type of device configured to capture images. The camera 312 may include one or more cameras. In some examples, the camera 312 may be configured to capture images of an object or user interacting with an application. For example, the camera 312 may be configured to capture images of a user or person physically gesticulating in free-space (e.g. the air surrounding the user), or otherwise interacting with an application within the field of view of the camera 312.

The camera 312 may be a stereo camera, a time-of-flight camera, or any other camera. For instance the camera 312 may be an image detector capable of sampling a background image in order to detect motions and, similarly, gestures of a user. The camera 312 may produce a grayscale image, color image, or a distance image, such as a stereo camera or time-of-flight camera capable of generating a distance image. A stereo camera may include two image sensors that acquire images at slightly different viewpoints, where a processor compares the images acquired from different viewpoints to calculate the distance of parts of the images. A time-of-flight camera may include an emitter that generates a pulse of light, which may be infrared light, where the time the pulse of light travels from the emitter to an object and back to a sensor is measured to calculate the distance of parts of the images.

Although the camera 312 may be a separate unit (such as a webcam) that communicates with the device 300, in other implementations the camera 312 is built into the device 300, and communicates with other components of the device 300 (such as the processor 302) via an internal bus.

A number of input devices 306 may interface with the device 300, such as a keyboard, mouse, trackball, pointing device, joystick, etc. The input devices 306 may also include audio- or video-capture devices (e.g., video cameras, microphones, etc.) and/or various sensors for sensing emissions (e.g., thermal, motion, sound, etc.). The input devices 306 may also include one or more data reading devices and/or input ports. Although FIG. 3 depicts input devices 306 as a single discrete element, the device 300 may include any number of dispersed input devices. For example, the device 300 may include a keyboard and a mouse as well as a video-capture device.

In one implementation, one or more input devices 306 (such as a video camera or an audio recording device) may be integrated with the display 310. One example of such an integrated unit is the VIEWSONIC® VX2255wmb multi-function HD LCD monitor commercially available from Viewsonic Corporation, which includes a 22-inch widescreen LCD display and an integrated 1.3 megapixel webcam with microphone. A user of device 300 may input commands to control and operate the processor 302 by way of the display 310 and input devices 306. These commands may be input by way of user movement, such as hand gestures, and/or by way of user manipulation of physical controls. For example, a video camera integrated in the display 310 may detect user movement, such as hand gestures, and interpret such movement as input commands to the processor 302. In this fashion, a user may interact with the processor 302 without needing to manipulate physical controls, such as a keyboard or mouse.

Alternatively, however, a user may use a keyboard or mouse to enter commands. The user may input commands to select and manipulate graphics and text objects displayed on the display 310 in order to operate and control the device 300.

The device 300 is electrically connected to and in operable communication with, over a wireline or wireless pathway, the camera 312, the display 310, the speakers 308, and the input devices 306 and is configured to control the operation of the processor 302 to provide for the therapy applications 320. In one configuration, the device 300 uses the processor 302 or other control circuitry to execute therapy applications that provide for enhanced camera-based input.

The device 300 may be a personal computer (PC), set top box, a television, an ultra-mobile personal computer (UMPC), a mobile internet device (MID), a digital picture frame (DPF), a portable media player (PMP), a general-purpose computer (e.g., a desktop computer, a workstation, or a laptop computer), a server, a gaming device or console, or any other type of electronic device that includes a processor or other control circuitry configured to execute instructions, or any other apparatus that includes a user interface.

The mobile support structure 322 provides support for components of the device 300 and allows for system mobility. The mobile support structure 322 may be constructed with various materials, such as metals, alloys, woods, plastics (e.g., extruded acrylic, acrylonitrile butadiene styrene (ABS)), polymers (e.g., rubber), glass, fiberglass, carbon fiber, medium-density fiberboard (MDF), high-density fiberboard (HDF), etc. The mobile support structure 322 may provide various features, such as support arms for display screens, casters for mobility, shelves, keyboard trays, drawers, notebook holders, storage units, power strips, cable management features, etc. These features may be fixed or adjustable, depending on the implementation. In addition, the mobile support structure 322 may include an integrated power supply.

In one configuration, the mobile support structure 322 may be a mobile equipment cart, such as the NB300 Equipment Cart or NB400 Powered Equipment Cart commercially available from Newcastle Systems. The cart may include two shelves, each having for example a 75-pound capacity and being 24 inches in width and 22 inches in depth. The cart may also include a pair of front casters and a pair of rear casters. The casters may, for example, be 5 inches in diameter. The front casters may be fixed, and the rear casters may offer locking and swivel features. Additionally, the cart may include or accommodate a power supply that includes, for example, one or more rechargeable batteries.

The one or more therapy applications 320 may be stored in the application database 318. The application database may be encoded in the storage medium 304. The matrix 316, which may also be encoded in the storage medium 304, may map or include associations between the various therapy applications 320 and user conditions and/or attributes. The therapy applications 320 may include music therapy applications, sensory applications, or immersive gaming applications, to name a few examples.

The therapy applications 320 include various applications that facilitate interaction with a user and generate visual and/or audible feedback to the user. Music applications may include various music-based, interactive applications that provide musical instruction and/or therapy. For example, musical applications may include a composition application that allows body movements to be translated into music. Such a composition application may enable the user to play a single note, or an entire song, by way of simple gesture movements. Notes and instruments may be customized for use with various tunes or ranges of motion.

The musical composition application may be configured to enable a user to create and play simple and complex musical instrument applications, all through gesture movement. Its primary features may include, for example, a full note selection via a full piano keyboard, a wide selection of musical instruments (e.g., 128 different instruments), interactive object selection and creation, object size variability, object color variability, touch sensitivity, object positioning, volume control, metronome and session save capability. The therapeutic benefits of this application may be optimally realized when used with the guidance of a registered therapist, and the program may be complementary to most music and physical therapy programs.

Another type of musical application may provide an introduction to musical sounds and musical movement. Such a musical introduction application may, for example, include several different multi-level applications involving interactive and low impact music creation, each controlled with hand coordination and rhythmic movement. The program may serve to stimulate low impact activity and the ability to create music and follow musical notes based on observation and recall.

One exemplary musical introduction application may enable the player to make animals displayed on the display 310 respond by touching them. It may also test memory skills following a pre-programmed sequence of sounds. Another musical introduction application may include a dance application, which may provide low impact activation and rhythmic movement to the beat of different types of musical songs. The player may use hand motions to activate the program features. The application may allow the player to follow musical notes and touch moving colored hands as traveling notes reach the player. As the player progresses and is able to match the movement of the notes, they will find that they are actually moving to the rhythm of the music. Yet another musical introduction application may be a percussion application. The player may interact and make rhythmic beats by touching the instrument or following a sequenced pattern. A horn application may also be provided, which may enable the player to either make music by touching displayed horns that surround their image or test their memory skills by following preprogrammed musical notes.

Immersive gaming applications may include applications that promote patient motivation and activation through gesture controlled immersive play. Gaming applications may include a variety of games that provide low impact stimulation and improve hand-eye coordination. The user may be immersed in different virtual worlds and may be able to interact with their surroundings in a variety of achievement-based, action-oriented gaming environments.

Immersive gaming applications may include one or more, or a combination of, interactive sport-based and skill-based games. In one exemplary skill-based game, the player tries to deflect displayed coconuts into a set of numbered baskets along the side of the screen. The objective is to see how many coconuts the player may get into the baskets. Using hand, arm or head movements, the player may deflect or knock the coconuts towards the baskets.

In another interactive game, the player is immersed in a carnival-like environment, and is able to juggle virtual balls as they descend from above. The more the player is able to keep the balls in the air, the more balls will appear. This application may be especially beneficial for use with stroke patients. In another example interactive game, a player fends off ninja fighters in different scenarios. Players may defend themselves by moving their hands and arms. Slight movement of the head and upper body may also be incorporated into the game.

Other immersive gaming applications may attempt to stimulate both cognitive and physical activation as well as encourage reaching and controlled movement. In one example, players are immersed in an environment that fills with balloon like objects. A subtle touch turns them into birds, while a hard touch causes the balloons to explode. The challenge of the game is to gently release the birds from all the objects. This application may be especially effective for rehabilitating stroke and cerebral palsy patients. In another example, the player is immersed in a space capsule, and through subtle upper body movements the player may move the capsule throughout the virtual world. Hand gestures enable the player to gain additional points.

Immersive gaming applications may additionally include various interactive sports-based games. Immersive gaming applications may include a soccer game, which immerses the player into a soccer goal net where they are challenged to stop incoming soccer balls. This game provides low impact upper extremity activation as the player must try to stop the balls from entering the net. Another game may be volleyball, which immerses the player onto a sandy beach court where they are able to bump, set and spike a virtual volleyball. Volleyball offers low impact upper extremity activation in a sports-like setting. Various other games may also be provided.

Sensory applications may include applications designed to promote relaxation, sensory stimulation and low impact activation through immersion in a variety of virtual environments. The user interacts with relaxed virtual surroundings through simple movements and gestures. Sensory applications may combine motion with sensory stimulation through music and visual special effects. Players are immersed into different relaxing environments that include swimming underwater, floating in space, moving through fog, wiping away mist, and interacting with various objects. These programs may promote low impact activation and relaxation.

One exemplary sensory application allows players to touch displayed planets, causing them to move away and then they come back to their original position. In another sensory application, players touch a displayed grid of squares to cause the squares of the grid to move away from the player. Another sensory application might allow the user to use various motions to push away clouds and cause water to ripple. In yet another example, user motion may cause displayed asteroids to explode or trigger a meteor shower.

FIG. 4 is a flowchart illustrating a computer-implemented process 400 that effects a therapy application using recognized gestures. Briefly, the computer-implemented process 400 includes accessing images of a user, selecting a therapy application appropriate for assisting in physical or cognitive rehabilitation of the user, invoking the therapy application, recognizing a gesture of the user from the accessed images, and controlling the invoked therapy application based on the recognized gesture.

In further detail, when the process 400 begins (S401), images of a user are accessed (S402). For example, first and second images captured by a camera may be accessed. The first and second images may be derived from individual image snapshots or from a sequence of images that make up a video sequence. Each image captures position information that allows an application to determine a pose or gesture of a user.

Next, a therapy application appropriate for assisting in physical or cognitive rehabilitation of the user is selected (S404). A therapy application may be, for example, a music therapy application, a sports therapy application, or an immersive gaming therapy application. A therapy application may be selected manually (e.g., by a user or a medical professional, using a user interface). A therapy application may also be selected based on a user's therapy prescriptions.

In addition to manually selecting a therapy application, a therapy application may also be automatically selected based on a determined medical condition of the user. Various approaches may be used to determine a user's medical condition. For example, an identity of the user may be determined based on performing facial detection and recognition on one of the accessed images, and a database (e.g., hospital database) may be queried to determine a medical condition associated with the user.

As another example, a medical appliance may be recognized in one of the accessed images. For example, a cast, wheel chair, etc. may be recognized and a medical condition may be determined based on the recognized medical appliance. A user's medical condition may also be determined based on information retrieved from accessed images or portions of images. For example, a medical chart may be recognized in the accessed images, optical character recognition may be performed on the image of the medical chart, and one or more words may be recognized, and the words may be matched to a medical condition.

A determined medical condition may be used as input to a matrix correlating therapy applications with medical conditions and therapeutic effects. A set of appropriate therapy applications may be accessed as an output of the matrix. A therapy application may be selected from the accessed set of therapy applications.

A therapy application may be selected from a candidate set of therapy applications via an avatar displayed on a user interface. For example, icons may be displayed adjacent to an avatar, where each icon represents a candidate therapy application. A gesture of the user may be recognized from the accessed images, and the avatar may be controlled based on the recognized gesture (e.g., if a user gestures leftward with their arm, an arm of the avatar may also move leftward). The candidate therapy application whose icon is affected by the controlled avatar may be outputted as the selected therapy application.

Therapy applications may be selected based on a detected presence of a required controller. For example, some therapy applications, such as a ping pong application, may require a special controller such as a ping pong paddle. From one of the accessed images, it may be recognized whether the user possesses a controller. If the user is recognized to possess the controller, a therapy application that requires possession of the controller may be selected. If the user is recognized to not possess the controller, a therapy application that does not require possession of the controller may be selected.

Returning to FIG. 4, after a therapy application has been selected, the therapy application is invoked (S406), where 'invoking' an application may include running, loading, or otherwise executing a software application. For example, the therapy application may be displayed on a user interface. Invoking a therapy application may involve configuration steps for a particular user. Configuration may include installing various software items, or positioning or aligning a display or camera to optimize images and user interaction. Additionally, invoking a therapy application may involve various access control and authentication procedures. For example, a user may be prompted to input authentication information, such as a password or various biometric information (e.g., fingerprints, hand measurements, etc.).

After the therapy application is invoked, a gesture of the user is recognized from the accessed images (S408). Generally, a gesture is intended to refer to a movement, position, pose, or posture that expresses an idea, opinion, emotion, communication, command, demonstration or expression. For instance, the user's gesture may be a single or multiple finger gesture; a single hand gesture; a single hand and arm gesture; a single hand and arm, and body gesture; a bimanual gesture; a head pose or posture; an eye position; a facial expression; a body pose or posture, or any other expressive body state. The user's gesture in a single image or between two images may be expressive of an enabling or "engagement" gesture.

The engagement gesture may be a specific hand pose or hand motion sequence gesticulated in a tracking region of a camera in front of a display that is held for a predetermined amount of time. One example gesture is a hand pose held in an upright position with all fingers and thumb spread apart widely. Another example is a circular hand motion made by extending the user's arm in front of their face, and moving their arm in a circle in front of their head. In essence, an engagement gesture specifies to the device that generates the user interface that the user is ready for further camera-based input to occur. To reduce errors, an engagement gesture may be an atypical gesture, such as a gesture that would not subconsciously be made with body language during an a normal conversation, or a gesture that would not be made in the ordinary performance of normal human activity.

Accordingly, from the two images, the gesture may be derived that defines an idea, opinion, emotion, communication, command, demonstration or expression of the user. For instance, the user's gesture may be a single or multiple finger gesture; a single hand gesture; a single hand and arm gesture; a single hand and arm, and body gesture; a bimanual gesture; a change in head pose or posture; a change in an eye position; a change in a facial expression; a change in a body pose or posture, or a transformation of any other expressive body state.

For brevity, the body part or parts used to perform relevant gestures are generally referred to as a "control object." For instance, the user may express a command using their entire body or with other physical objects, in which case their entire body or the other physical objects may be the control object. A user may more subtly express a command by blinking their eye, by flaring their nostrils, or by wiggling a finger, in which case the eyelid, nose, or finger may be the control object. The user's gesture in a single image or between two images may be expressive of an enabling or "engagement" gesture. A control object may also be a physical device, such as an infrared finger light, a retro-reflector, or a remote control.

There are many ways of determining a user's gesture from a camera image. For instance, the gesture of "drawing a circle in the air" or "swiping the hand off to one side" may be detected by a gesture analysis and detection process using the hand, arm, body, head or other object position information. Although the gesture may involve a two- or three-dimensional position displacement, such as when a swiping gesture is made, in other instances the gesture includes a transformation without a concomitant position displacement. For instance, if a hand is signaling "stop" with five outstretched fingers and palm forward, the gesture of the user changes if all five fingers are retracted into a ball with the palm remaining forward, even if the overall position of the hand or arm remains static.

Gestures may be detected using heuristic techniques, such as by determining whether the hand position information passes explicit sets of rules. For example, the gesture of "swiping the hand off to one side" may be identified if the following gesture detection rules are satisfied: (1) the change in horizontal position is greater than a predefined distance over a time span that is less than a predefined limit; (2) the horizontal position changes monotonically over that time span; (3) the change in vertical position is less than a predefined distance over that time span; and (4) the position at the end of the time span is nearer to (or on) a border of the hand detection region than the position at the start of the time span.

Some gestures utilize multiple rule sets that are executed and satisfied in an explicit order, where the satisfaction of a rule set causes a system to change to a state where a different rule set is applied. This system may be unable to detect subtle gestures, in which case Hidden Markov Models may be used, as these models allow for chains of specific motions to be detected, but also consider the overall probability that the motions sufficiently fit a gesture.

Criteria may be used to filter out irrelevant or unintentional candidate gestures. For example, a plane may be defined at a predetermined distance in front of a camera, where gestures that are made or performed on the far side of the plane from the camera are ignored, while gestures or potential gestures that are performed between the camera and the plane are monitored, identified, recognized, filtered, and processed as appropriate. The plane may also be defined relative to another point, position or object, such as relative to the user's torso. Furthermore, the enhanced approach described herein may use a background filtering model to remove background images or objects in motion that do not make up the control object.

In addition to recognizing gestures or changes in gestures, other information may also be determined from the images. For example, a facial detection and recognition process may be performed on the images to detect the presence and identity of users within the image. Identity information may be used, for example, to determine or select available options, types of available interactions, or to determine which of many users within an image is to be designated as a controlling user if more than one user is attempting to engage the input functionality.

So as to enable the input of complex commands and to increase the number of input options, the process for recognizing the user's gesture may further include recognizing a first displacement in a first direction, and recognizing a second displacement in a second direction, and aggregating these multiple displacements as a single gesture. Furthermore, the recognition of the user's gesture may determine a magnitude and direction of the user's gesture.

Returning to FIG. 4, the invoked therapy application is controlled based on the recognized gesture (S410), thereby ending the process 400 (S412). For example, a representation of a user displayed in a virtual environment may be moved within the virtual environment in a magnitude and direction correlating to the determined magnitude and direction of the gesture. Visual and/or audible feedback may be provided to the user based on moving the representation.

As another example, the invoked therapy application may be started or stopped in response to a particular gesture, such as a wave. A virtual object in a virtual world defined by the therapy application may be interacted with. For example, a user may perform gestures which simulate juggling, and virtual objects (e.g., colored balls or bowling pins) may be "virtually juggled" (e.g., caught and tossed into the air by an avatar).

Other examples of application control include enabling a user to play a song or portion of a song using the recognized gesture or mapping the recognized gesture to a mouse event, such as a mouse click or drag.

Figure 5A:
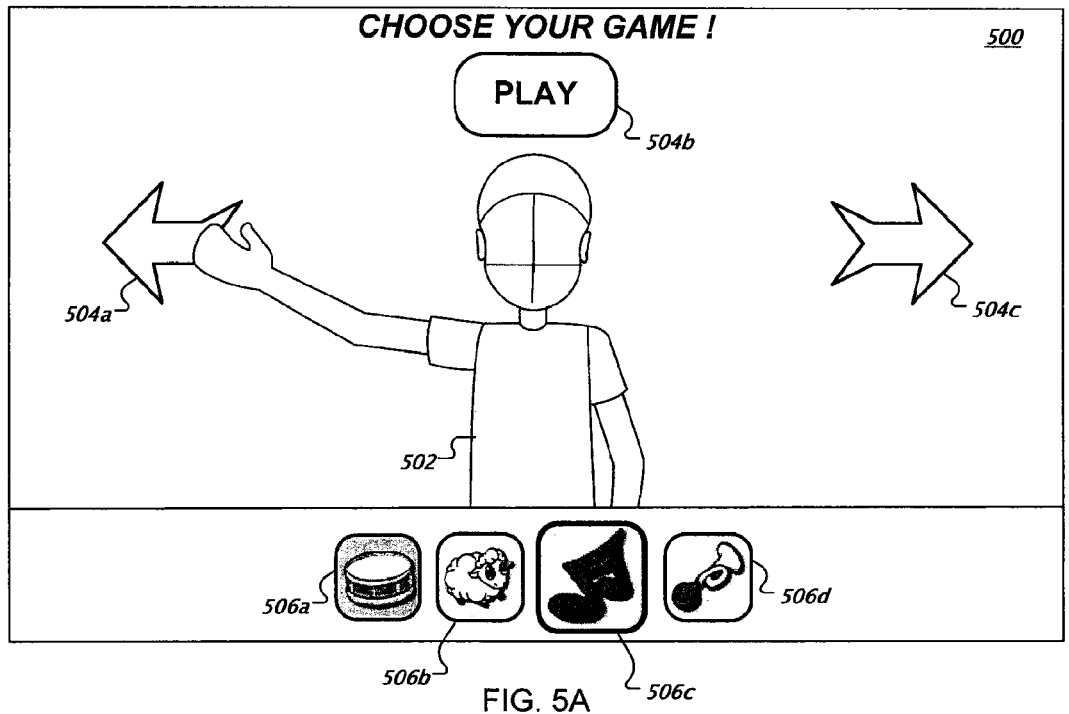
FIGS. 5A-B illustrate exemplary gestures and concomitant user interface interactions.
Figure 5B:
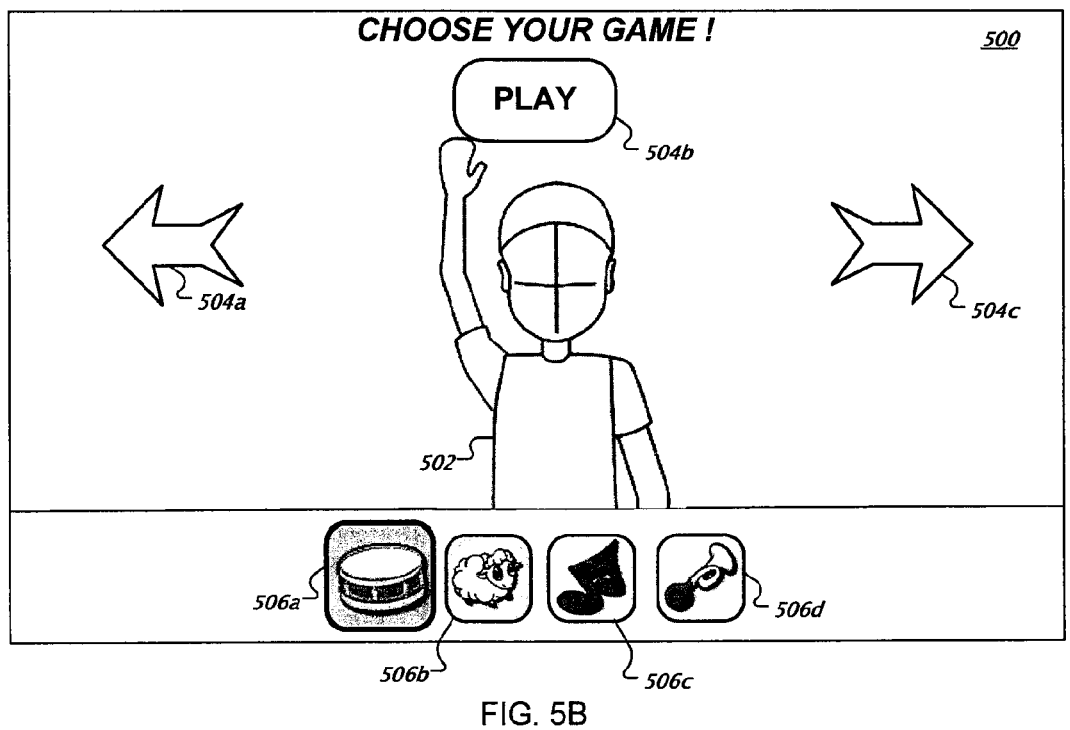

FIGS. 5A-B illustrate an interface 500 for selecting a therapy application. The interface 500 includes a user image 502. The user image 502 may be a live video image of the user or may be an avatar representing the user. Interaction objects 504a, 504b, and 504c are displayed adjacent to the user image 502. The interface 500 includes icons 506 representing candidate therapy applications. For example, the icons 506 include an icon 506a representing a drums therapy application, an icon 506b representing a "farm animals" therapy application, an icon 506c representing a dance therapy application, and an icon 506d representing a music application.

The user may gesture so that a hand of the user image 502 moves over one of the interaction elements 504a-c. Interaction element 504b may be used to select a candidate therapy application 506. Interaction elements 504a and 504c may be used to scroll through candidate therapy applications 506. Interaction element 504a represents a left direction and interaction element 504c represents a right direction.

The user may move their hand over the interaction element 504a or 504c to scroll the candidate therapy applications 506 until the icon representing the desired application is highlighted. For example, in FIG. 5A, the icon 506c representing a dance therapy application is highlighted. In FIG. 5B, the icon 506a representing the drums therapy application is highlighted. Once the desired icon has been highlighted, the user may wave their hand so that a hand of the user image 502 moves over the interaction element 504b to invoke the selected application.

FIG. 6 depicts an exemplary table 600 representing information included in the matrix 316 (FIG. 3). As illustrated in FIG. 6, table 600 may include a listing 605 of various therapy applications 320 (FIG. 3). Table 600 may map or correlate these applications with various physical therapies 610 and cognitive therapies 620. For example, a table column 630 indicates that a soccer application is appropriate for the following physical therapies: lower back, legs, foot/ankles, side-to-side, balance, postural control, and weight shifting. Additionally, the column 630 indicates that the soccer application is appropriate for the following cognitive therapies: learning, achievement/mastery, audio/visual stimulation, perceptual motor skills, sensory motor skills, variety, concentration, and selection recognition.

Figure 7A:
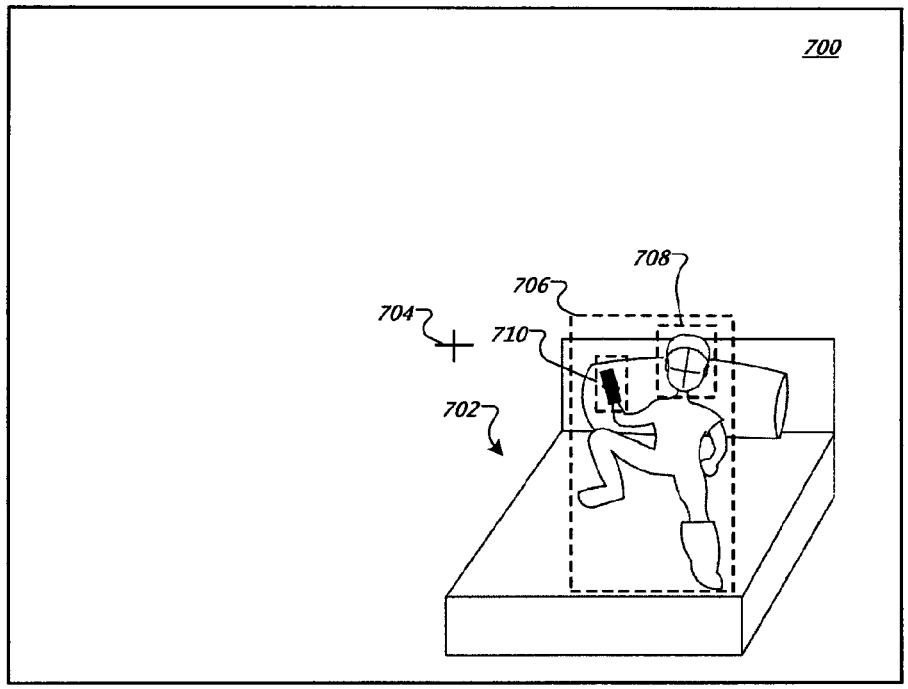
FIGS. 7A-B illustrate an alignment process.
Figure 7B:
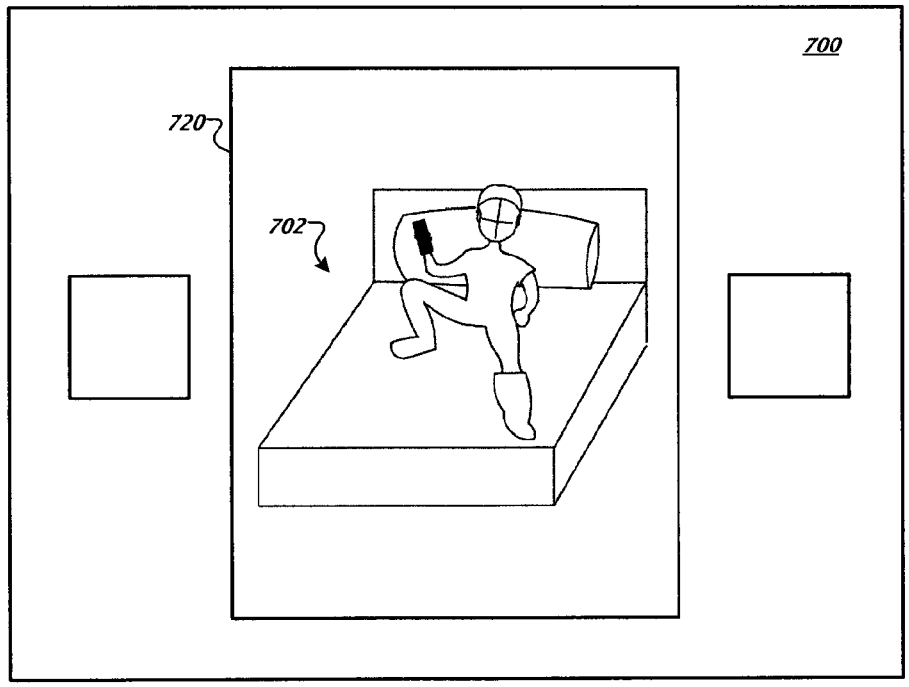

FIGS. 7A-B illustrate an alignment process. The therapy device 200 (discussed above with respect to FIG. 2) is a portable device that may be wheeled into a hospital room, placed in front of a bed, placed in front of a patient in a wheelchair, etc. The therapy device 200 may be used with multiple patients and may be moved from patient to patient. The portability and multiple patient use of the therapy device 200 may mean that the therapy device 200 is not always aligned when first moved into a new location. For example and as shown in FIG. 7A, upon being wheeled into a patient's hospital room, an image 702 captured by the therapy device's camera may be off-center as displayed in a user interface 700 (i.e., the image 702 is to the right and below a center-of-screen mark 704).

An alignment process may be performed to align and/or crop a captured image. For example, from portions 706, 708, and 710 of a captured image, the face, controller, or torso of a user may be identified, and the captured image may be aligned and/or cropped so that the image of the user is displayed in the center of a user interface, or centered within a region 720 of a user interface, as illustrated in FIG. 7B.

Figure 8:
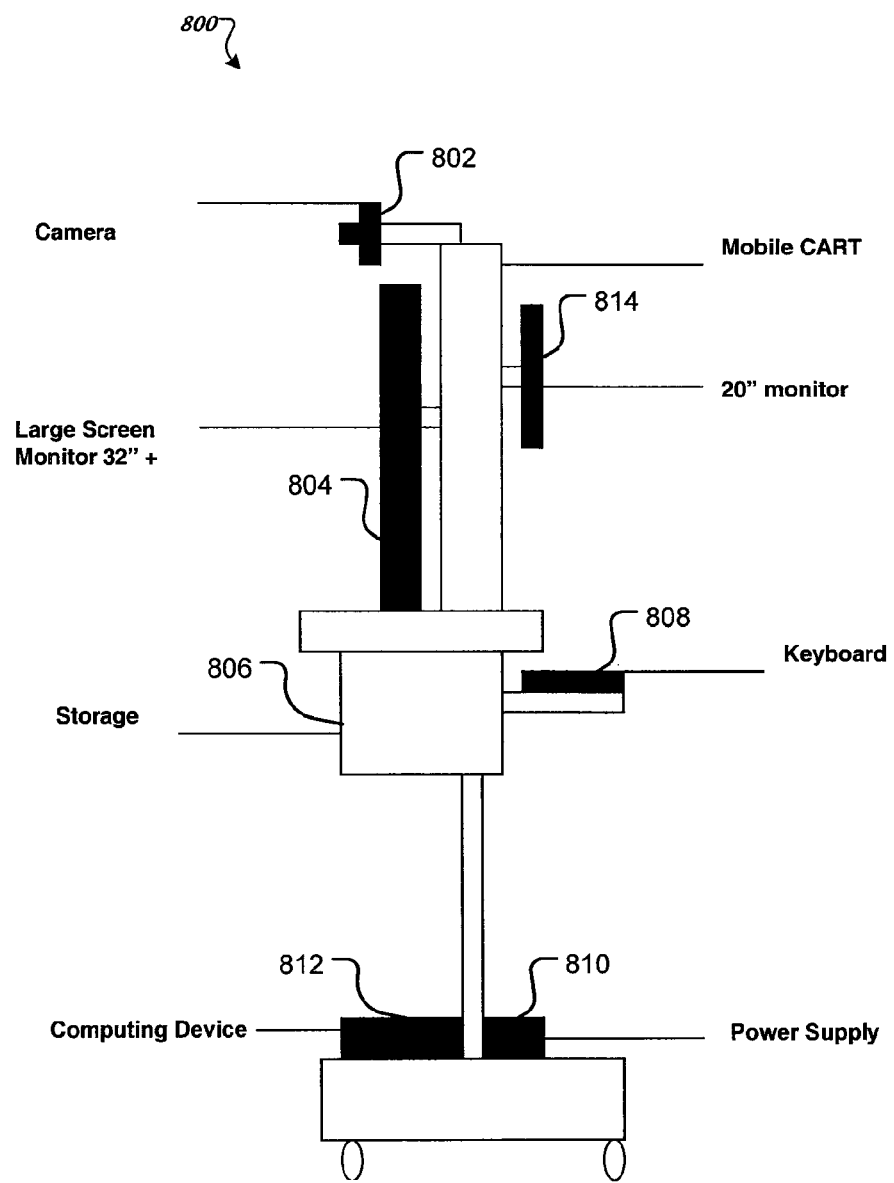

FIG. 8 illustrates an alternative implementation of a therapy device 800. Similar to the therapy device 200 (FIG. 2), the therapy device 800 includes a camera 802, display 804, storage area 806, keyboard 808, power supply 810, and computing device 812. The therapy device 800 also includes a second display 814 on the opposite side of the therapy device from the display 804. The second display 814 may be used by a therapist or medical professional. The second display 814 may be used to display interfaces of applications used to configure the therapy device before use by a patient or status applications such as progress and summary reports. The second display 814 may also be used to display a mirror view of the display 804 to a therapist while the patient is using the therapy device 800.

Figure 9:
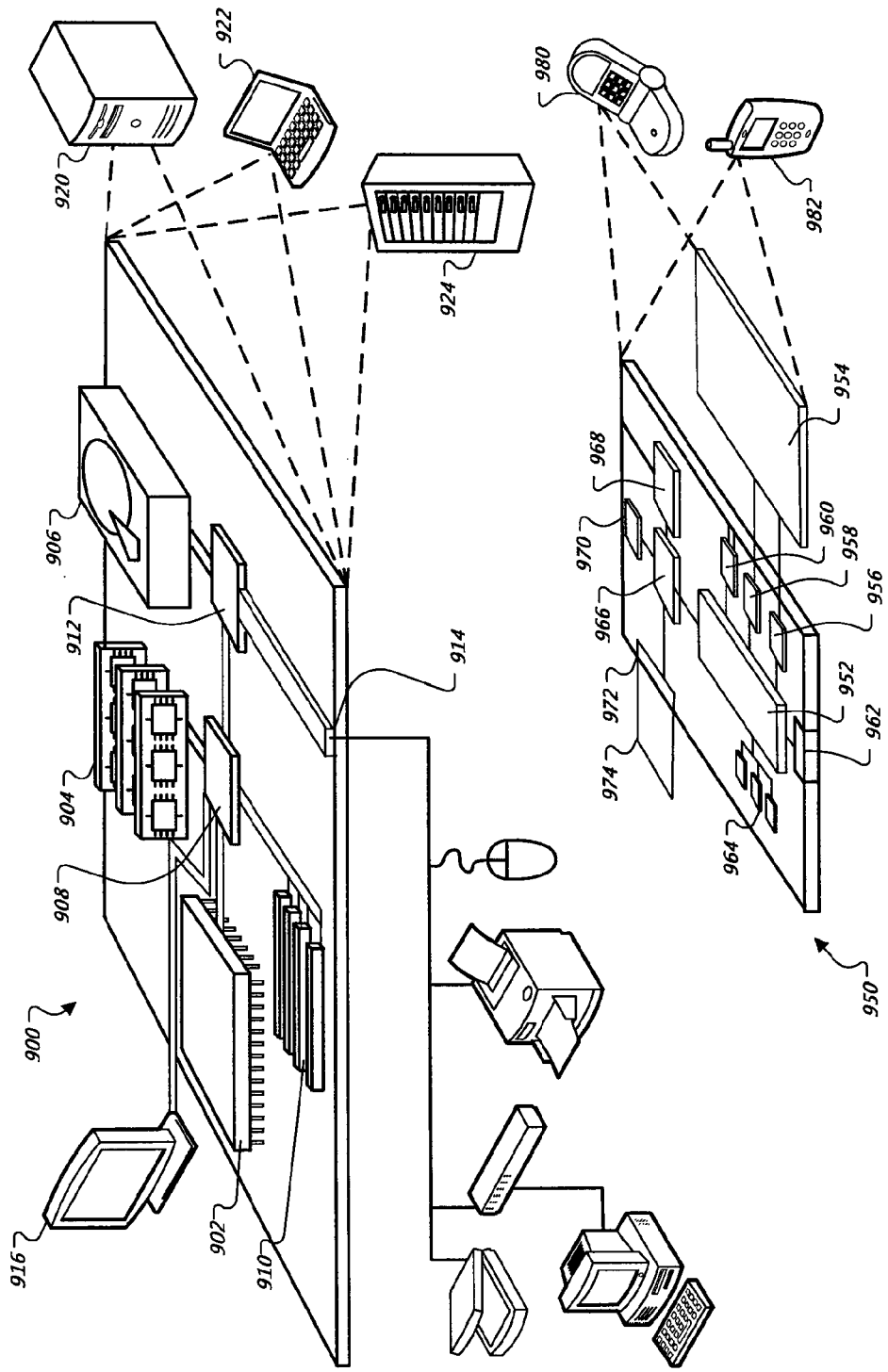
FIG. 9 illustrates an exemplary computing device.
Like reference numbers represent corresponding parts throughout.

FIG. 9 is a block diagram of computing devices 900, 950 that may be used to implement the systems and methods described in this document, as either a client or as a server or plurality of servers. Computing device 900 is intended to represent various forms of digital computers, such as laptops, desktops, workstations, personal digital assistants, servers, blade servers, mainframes, and other appropriate computers. Computing device 950 is intended to represent various forms of mobile devices, such as personal digital assistants, cellular telephones, smartphones, and other similar computing devices. The components shown here, their connections and relationships, and their functions, are meant to be exemplary only, and are not meant to limit the implementations described and/or claimed in this document.

Computing device 900 includes a processor 902, memory 904, a storage device 906, a high-speed interface 908 connecting to memory 904 and high-speed expansion ports 910, and a low speed interface 912 connecting to low speed bus 914 and storage device 906. Each of the components 902, 904, 906, 908, 910, and 912, are interconnected using various busses, and may be mounted on a common motherboard or in other manners as appropriate. The processor 902 may process instructions for execution within the computing device 900, including instructions stored in the memory 904 or on the storage device 906 to display graphical information for a GUI on an external input/output device, such as display 916 coupled to high speed interface 908. In other implementations, multiple processors and/or multiple buses may be used, as appropriate, along with multiple memories and types of memory. Also, multiple computing devices 900 may be connected, with each device providing portions of the necessary operations (e.g., as a server bank, a group of blade servers, or a multi-processor system).

The memory 904 stores information within the computing device 900. In one implementation, the memory 904 is a computer-readable medium. In one implementation, the memory 904 is a volatile memory unit or units. In another implementation, the memory 904 is a non-volatile memory unit or units. The storage device 906 is capable of providing mass storage for the computing device 900. In one implementation, the storage device 906 is a computer-readable medium. In various different implementations, the storage device 906 may be a floppy disk device, a hard disk device, an optical disk device, or a tape device, a flash memory or other similar solid state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 904, the storage device 906, memory on processor 902, or a propagated signal.

The high speed controller 908 manages bandwidth-intensive operations for the computing device 900, while the low speed controller 912 manages lower bandwidth-intensive operations. Such allocation of duties is exemplary only. In one implementation, the high-speed controller 908 is coupled to memory 904, display 916 (e.g., through a graphics processor or accelerator), and to high-speed expansion ports 910, which may accept various expansion cards (not shown). In the implementation, low-speed controller 912 is coupled to storage device 906 and low-speed expansion port 914. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 900 may be implemented in a number of different forms, as shown in the figure. For example, it may be implemented as a standard server 920, or multiple times in a group of such servers. It may also be implemented as part of a rack server system 924. In addition, it may be implemented in a personal computer such as a laptop computer 922. Alternatively, components from computing device 900 may be combined with other components in a mobile device (not shown), such as device 950. Each of such devices may contain one or more of computing device 900, 950, and an entire system may be made up of multiple computing devices 900, 950 communicating with each other.

Computing device 950 includes a processor 952, memory 964, an input/output device such as a display 954, a communication interface 966, and a transceiver 968, among other components. The device 950 may also be provided with a storage device, such as a microdrive or other device, to provide additional storage. Each of the components 950, 952, 964, 954, 966, and 968, are interconnected using various buses, and several of the components may be mounted on a common motherboard or in other manners as appropriate.

The processor 952 may process instructions for execution within the computing device 950, including instructions stored in the memory 964. The processor may also include separate analog and digital processors. The processor may provide, for example, for coordination of the other components of the device 950, such as control of user interfaces, applications run by device 950, and wireless communication by device 950.

Processor 952 may communicate with a user through control interface 958 and display interface 956 coupled to a display 954. The display 954 may be, for example, a TFT LCD display or an OLED display, or other appropriate display technology. The display interface 956 may comprise appropriate circuitry for driving the display 954 to present graphical and other information to a user. The control interface 958 may receive commands from a user and convert them for submission to the processor 952. In addition, an external interface 962 may be provide in communication with processor 952, so as to enable near area communication of device 950 with other devices. External interface 962 may provide, for example, for wired communication (e.g., via a docking procedure) or for wireless communication (e.g., via Bluetooth or other such technologies).

The memory 964 stores information within the computing device 950. In one implementation, the memory 964 is a computer-readable medium. In one implementation, the memory 964 is a volatile memory unit or units. In another implementation, the memory 964 is a non-volatile memory unit or units. Expansion memory 974 may also be provided and connected to device 950 through expansion interface 972, which may include, for example, a SIMM card interface. Such expansion memory 974 may provide extra storage space for device 950, or may also store applications or other information for device 950. Specifically, expansion memory 974 may include instructions to carry out or supplement the processes described above, and may include secure information also. Thus, for example, expansion memory 974 may be provide as a security module for device 950, and may be programmed with instructions that permit secure use of device 950. In addition, secure applications may be provided via the SIMM cards, along with additional information, such as placing identifying information on the SIMM card in a non-hackable manner.

The memory 964 may include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 964, expansion memory 974, memory on processor 952, or a propagated signal.

Device 950 may communicate wirelessly through communication interface 966, which may include digital signal processing circuitry where necessary. Communication interface 966 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 968. In addition, short-range communication may occur, such as using a Bluetooth, WiFi, or other such transceiver (not shown). In addition, GPS receiver module 970 may provide additional wireless data to device 950, which may be used as appropriate by applications running on device 950.

Device 950 may also communication audibly using audio codec 960, which may receive spoken information from a user and convert it to usable digital information. Audio codex 960 may likewise generate audible sound for a user, such as through a speaker, e.g., in a handset of device 950. Such sound may include sound from voice telephone calls, may include recorded sound (e.g., voice messages, music files, etc.) and may also include sound generated by applications operating on device 950.

The computing device 950 may be implemented in a number of different forms, as shown in the figure. For example, it may be implemented as a cellular telephone 980. It may also be implemented as part of a smartphone 982, personal digital assistant, or other similar mobile device.

Various implementations of the systems and techniques described here may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal.

The term "machine-readable signal" refers to any signal used to provide machine instructions and/or data to a programmable processor.

To provide for interaction with a user, the systems and techniques described here may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The systems and techniques described here may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the systems and techniques described here), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

A number of implementations have been described. Nevertheless, it will be understood that various modifications may be made without departing from the spirit and scope of the disclosure. Accordingly, other implementations are within the scope of the following claims.

What is claimed is:

1. A method comprising:
    recognizing, by a computing device, whether a user possesses a controller based on information from a capture device;
    executing, by the computing device, an application based on possession of the controller, if it is recognized the user possesses the controller; and
    selecting an application that does not require possession of the controller, if it is not recognized that the user possesses the controller;
    wherein selecting the application includes:
    displaying a plurality of icons, each icon representing a candidate application, adjacent to an avatar;
    recognizing, from a plurality of captured images, a gesture of the user;
    controlling the avatar based on the recognized gesture; and
    outputting, as the selected application, one of the candidate applications, wherein an icon corresponding to the one candidate application is affected by the controlled avatar.

2. The method of claim 1, wherein the capture device comprises a camera.

3. The method of claim 1, wherein the application is a therapy application appropriate for assisting in physical or cognitive rehabilitation of the user.

4. The method of claim 1, further comprising:
    recognizing a gesture of the user based on the information; and
    controlling the executed application based on the recognized gesture.

5. The method of claim 4,
    wherein executing the selected application includes:
    generating a virtual environment; and
    displaying a representation of the user within the virtual environment,
    wherein recognizing the gesture further comprises recognizing a magnitude and direction of the gesture, and
    wherein controlling the executed application includes:
    moving the representation within the virtual environment in a magnitude and direction correlating to the determined magnitude and direction of the gesture; and
    providing visual or audible feedback to the user based on moving the representation.

6. The method of claim 1, further comprising:
    determining, by the computing device, a medical condition of the user,
    wherein the application is selected based on the determined medical condition.

7. The method of claim 6, wherein the information comprises a captured image, and wherein the medical condition is determined based at least in part on the captured image.

8. The method of claim 7, wherein the medical condition is determined based at least in part on facial recognition performed on the captured image, a medical chart or label identified in the captured image, or a medical appliance recognized in the captured image.

9. The method of claim 6, wherein selecting an application includes:
    accessing a matrix correlating applications with medical conditions and therapeutic effects;
    inputting the determined medical condition or a desired therapeutic effect remedying the determined medical condition into the matrix;
    accessing, as an output of the matrix, a set of applications correlating to the determined medical condition or the desired therapeutic effect; and
    selecting the application from the accessed set of applications.

10. The method of claim 6, wherein determining a medical condition of the user includes:
    determining an identity of the user based on performing facial detection and recognition of one of the captured images; and
    querying a database that correlates users with medical conditions, using the determined identity.

11. A non-transitory computer-readable medium storing instructions that, when executed, cause a computing device to:
    recognize whether a user possesses a controller based on information from a capture device;
    execute an application based on possession of the controller, if it is recognized the user possesses the controller; and
    select an application that does not require possession of the controller, if it is not recognized that the user possesses the controller;
    wherein the instructions that cause the computing device to select the application include additional instructions that further cause the computing device to:
    display a plurality of icons, each icon representing a candidate application, adjacent to an avatar;

recognize, from a plurality of captured images, a gesture of the user;
control the avatar based on the recognized gesture; and
output, as the selected application, one of the candidate applications, wherein an icon corresponding to the one candidate application is affected by the controlled avatar.

12. The non-transitory computer-readable medium of claim 11, wherein the capture device comprises a camera.

13. The non-transitory computer-readable medium of claim 11, wherein the application is a therapy application appropriate for assisting in physical or cognitive rehabilitation of the user.

14. The non-transitory computer-readable medium of claim 11, having additional instructions stored thereon that, when executed, further cause the computing device to:
recognize a gesture of the user based on the information; and
control the executed application based on the recognized gesture.

15. The non-transitory computer-readable medium of claim 11, having additional instructions stored thereon that, when executed, further cause the computing device to:
determine a medical condition of the user,
wherein the application is selected based on the determined medical condition.

16. An apparatus comprising:
at least one processor; and
memory storing computer-readable instructions that, when executed by the at least one processor, cause the apparatus to:
recognize whether a user possesses a controller based on information from a capture device;
execute an application based on possession of the controller, if it is recognized the user possesses the controller; and
select an application that does not require possession of the controller, if it is not recognized that the user possesses the controller;
wherein the instructions that cause the apparatus to select the application include instructions that further cause the apparatus to:
display a plurality of icons, each icon representing a candidate application, adjacent to an avatar;
recognize, from a plurality of captured images, a gesture of the user;
control the avatar based on the recognized gesture; and
output, as the selected application, one of the candidate applications, wherein an icon corresponding to the one candidate application is affected by the controlled avatar.

17. The apparatus of claim 16, wherein the capture device comprises a camera.

18. The apparatus of claim 16, wherein the application is a therapy application appropriate for assisting in physical or cognitive rehabilitation of the user.

19. The apparatus of claim 16, wherein the memory stores additional computer-readable instructions that, when executed by the at least one processor, further cause the apparatus to:
recognize a gesture of the user based on the information; and
control the executed application based on the recognized gesture.

20. The apparatus of claim 16, wherein the memory stores additional computer-readable instructions that, when executed by the at least one processor, further cause the apparatus to:
determine a medical condition of the user,
wherein the application is selected based on the determined medical condition.

21. A system comprising:
means for recognizing whether a user possesses a controller based on information from a capture device;
means for executing an application based on possession of the controller, if it is recognized the user possesses the controller; and
means for selecting an application that does not require possession of the controller, if it is not recognized that the user possesses the controller;
wherein the means for selecting the application includes:
means for displaying a plurality of icons, each icon representing a candidate application, adjacent to an avatar;
means for recognizing, from a plurality of captured images, a gesture of the user;
means for controlling the avatar based on the recognized gesture; and
means for outputting, as the selected application, one of the candidate applications, wherein an icon corresponding to the one candidate application is affected by the controlled avatar.

22. The system of claim 21, wherein the capture device comprises a camera.

23. The system of claim 21, wherein the application is a therapy application appropriate for assisting in physical or cognitive rehabilitation of the user.

24. The system of claim 21, further comprising:
means for recognizing a gesture of the user based on the information; and
means for controlling the executed application based on the recognized gesture.

25. A device comprising:
means for accessing images of a user;
means for selecting a therapy application appropriate for assisting in physical or cognitive rehabilitation or therapy of the user;
means for invoking the therapy application;
means for recognizing a gesture of the user from the accessed images; and
means for controlling the invoked therapy application based on the recognized gesture;
wherein the means for selecting the therapy application comprises:
means for recognizing, from one or more of the images, whether the user possesses a controller; and
means for selecting a therapy application that does not require possession of the controller, if the user is recognized to not possess the controller;
wherein the means for selecting the therapy application includes:
means for displaying a plurality of icons, each icon representing a candidate application, adjacent to an avatar;
means for recognizing, from the images, a gesture of the user;
means for controlling the avatar based on the recognized gesture; and
means for outputting, as the selected therapy application, one of the candidate applications, wherein an icon corresponding to the one candidate application is affected by the controlled avatar.

* * * * *